United States Patent [19]

Wood et al.

[11] 4,294,855

[45] * Oct. 13, 1981

[54] EMOLLIENT AND/OR DYED PRILLED UREA BATH BEAD COMPOSITION

[75] Inventors: Donald C. Wood, Des Plaines; Robert L. McLaughlin, Wilmette, both of Ill.

[73] Assignee: DeSoto, Inc., Des Plaines, Ill.

[ * ] Notice: The portion of the term of this patent subsequent to Jun. 6, 1995, has been disclaimed.

[21] Appl. No.: 635,282

[22] Filed: Nov. 26, 1975

[51] Int. Cl.$^3$ .................................................. A61K 7/50
[52] U.S. Cl. ........................................ 424/358; 264/7; 264/13; 264/14; 424/63; 424/322; 424/364; 427/56.1
[58] Field of Search .................... 264/7, 13, 14, 15; 424/63, 322, 358, 364; 427/56

[56] References Cited

U.S. PATENT DOCUMENTS

| | | | |
|---|---|---|---|
| 1,734,260 | 11/1929 | Lamont | 264/14 |
| 3,196,079 | 7/1965 | Blaustein | 424/69 |
| 3,268,631 | 8/1966 | Price | 264/14 |
| 3,686,373 | 8/1972 | Griesheimer | 264/14 |
| 3,689,678 | 9/1972 | Fox | 424/365 |
| 3,798,179 | 3/1974 | Hellyer | 424/37 |
| 3,816,352 | 6/1974 | Loureiro | 252/556 |
| 3,851,065 | 11/1974 | Ludwig | 424/346 |
| 3,952,078 | 4/1976 | Bradley | 264/13 |
| 4,020,156 | 4/1977 | Murray | 424/76 |

FOREIGN PATENT DOCUMENTS 986416 3/1976 Canada .
2152810 6/1973 France .

OTHER PUBLICATIONS

Sagarin, Cos. Sci. & Tech. Intersci. Pub. NY, 1957, pp. 112–113, 161–162, 171–172, 720–721.
Otto, Chem. Abs. vol. 73, 1970, Ab. No. 112914q.

*Primary Examiner*—Anna P. Fagelson
*Attorney, Agent, or Firm*—Dressler, Goldsmith, Shore, Sutker & Milnamow

[57] ABSTRACT

A bath bead composition is disclosed based on urea beads in combination with at least one active bath component selected from germicides, emollients, and surfactants. The composition dissolves in water to provide an approximately neutral solution, and is not irritating to the skin.

9 Claims, No Drawings

EMOLLIENT AND/OR DYED PRILLED UREA BATH BEAD COMPOSITION

The present invention relates to bath bead compositions which are based upon the utilization of urea beads in combination with a small proportion of at least one active bath component selected from germicides, emollients, and surfactants.

At the present time, bath compositions are in the form of powders, with the particle size ranging from fine powders to coarse granules, and these are usually constituted by an alkaline detergent material, such as anhydrous sodium tripolyphosphate combined with small proportions of oils, perfumes, and dyes, to provide attractive coloration. Such products are occasionally irritating to portions of the human body due to the alkaline pH of the bath water, and the fact that individuals immerse themselves in these baths for prolonged periods of time. This is especially true when small children employ the baths under consideration. Difficulties commonly encountered are skin rashes, and less severe skin irritations inducing an itchy feeling.

In this invention, an attractive beaded composition is provided which is useful at approximately neutral pH and which provides good emolliency without irritation to the skin or mucous membranes. The material is nontoxic if ingested and, since it is primarily constituted by beads, instead of powders, it presents a more bead-like appearance which is significant since the compositions are usually sold under the designation "bath beads".

The bath bead compositions in accordance with the present invention are primarily constituted by urea in bead form, such urea being known in the art as prilled urea. These beads are available in commerce, and are normally formed by heating urea, and dropping it through a tower so that the hot urea forms a generally spherical bead as it cools. The urea beads are combined with a minor proportion, generally from 0.1–25%, preferably from 0.5–15%, of the weight of the composition, of at least one active bath component selected from germicides, emollients, and surfactants. In preferred practice, an emollient, illustrated by mineral oil or similar oily ester, such as isopropyl myristate, is present since this enhances the emollient action which the urea has been found to provide. It is also normal to include a trace of dye for desired coloration, and a perfume for desired fragrance, but these peripheral ingredients, in general, constitute less than 2% of the weight of the composition. It is also desirable to include an anti-caking agent, such as hydrolyzed protein or water soluble corn starch, but it is possible to avoid the use of such agent.

Referring more particularly to the urea beads which constitute the bulk of the composition, it has already been pointed out that this form of urea is available under the designation prilled urea, which is a round, hard bead capable of absorbing the small amount of emollient oils that may be employed in a bath bead composition. Urea is nonirritating to the skin and mucous membranes and, if ingested, it acts as a diuretic, and is not harmful. In contrast, the sodium tripolyphosphate which is normally used provides a pH in the bath ranging from pH 9–pH 10.2. The Merck Index indicates that sodium tripolyphosphate is moderately irritating to the skin and mucous membranes and that ingestion can cause violent purging. The compositions of this invention, when dissolved in the bath in an amount to provide approximately 0.5% by weight, provide a bath pH in the range of 6–8, preferably 6.5–7.5, assuming that the water used in the bath is neutral to begin with.

The prilled urea in this invention should constitute at least 50% of the composition, more preferably at least 75% of the composition. In the absence of the surfactant component, the urea will desirably constitute at least 85% of the weight of the composition.

It should be noted that urea in powder form is not appropriate because it is strongly hygroscopic, whereas the prilled urea is only slightly hygroscopic. If the powdered urea and the emollient oil are combined so that the oil is absorbed into the powdered urea, the powdered urea containing the oil can be prilled by heating the same and dropping it through a prilling tower, so this should make it clear that the oil can be absorbed into the prilled urea either before or after prilling.

It is important to observe that the urea enhances the emollient action on the skin, and thus directly contributes to the skin soothing characteristics of the bath composition.

The prilled urea still retains a limited tendency to absorb moisture. The small amount of water absorbed or adsorbed on the urea beads is sufficient to pick up the small amounts of water soluble dye which are frequently used to provide desired coloration for the beads and for the water in the bath. This allows one to apply the dye by simply mixing the urea beads and the water soluble dye (in the form of a dry powder). The urea beads also possess a limited capacity to absorb an oily emollient or oily perfume, and these can be picked up by mixing for an extended period of time. It is possible to complete absorption of the oil components (which takes many hours) to eliminate the need for an anti-caking agent, but normally such agents are used.

The anti-caking agents which may be used include finely divided modified proteins, starches such as corn starch, and natural gums. Salts which absorb moisture by forming hydrides and which do not induce significant alkalinity in the small proportions utilized can also be incorporated, such as anhydrous sodium borax. Anti-caking agents are well known, per se, and while they are needed herein, their use is itself conventional, and they can be eliminated in many instances.

The use of anti-caking agents can also be avoided by encapsulating the oily emollient and/or dye in a water soluble powder absorbent such as a water soluble starch or dextrin.

Referring more particularly to the active bath components, these have been indicated to be selected from germicides, emollients, and surfactants, the emollients being preferred.

The emollients are oily materials and are subject to wide variation. Fatty derivatives of glycerin are common emollients, these being illustrated by glyceryl monostearate or laurate. Fatty acid alcohol esters generally are good emollients, such as isopropyl myristate or palmitate. Mineral oil can be used. Even high molecular weight alcohols can be used, such as cetyl or stearyl alcohol, or adducts thereof with from 1 to 4 mols of ethylene oxide. Modified lanolin alcohols are also useful, as are the adducts thereof with ethylene oxide. The emollient is preferably used in an amount of from 0.5–10% of the composition.

Germicides constitute a known class of materials which are useful in the compositions under consideration. Commercially available useful germicides are illustrated by Triclosan (Ciba Geigy) and Irgasan DP 300. The germicide would be used in an amount of from 0.1-3% of the composition.

The surfactants which may be used may vary considerably, but since a foaming action is usually desired to provide a bubble bath effect, anionic surfactants are preferred. The preferred anionic surfactant is an alpha olefin sulfonate. The alpha olefins which are preferred are the commercial mixtures of $C_{12}$-$C_{14}$ alpha olefins.

Indeed, any nonirritating high foaming solid detergent can be used, and these include sodium lauryl sulfate powder, magnesium lauryl sulfate powder, alpha olefin sulfonate flake or powder, nonyl phenyl sulfonate (flake or powder), or mixtures of these materials. Thus, the preferred surfactants are solid anionic surfactants, more particularly sulfates and sulfonates. If the detergent is encapsulated, then liquid detergents are useful.

The foaming surfactant is used in an amount of from about 2% to about 15% of the weight of the composition.

Either in the presence or absence of the high foaming surfactant, tests indicate that no oily film or ring is left in the bathtub after continued use of the compositions of this invention. These compositions are also not affected by hard water which would usually form scums on or in the bath water.

The invention is illustrated in the following examples.

| NONFOAMING BATH BEAD COMPOSITION | |
| --- | --- |
| Component | Parts by Weight |
| Prilled urea | 92.4 |
| Isopropyl myristate | 2.0 |
| Hydrolyzed protein | 5.0 |
| Trace dye for color | 0.1 |
| Perfume | 0.5 |
| | 100.0 |

| CHILDREN'S BUBBLE BATH | |
| --- | --- |
| Component | Parts by Weight |
| Prilled urea | 90.3 |
| Alpha olefin ($C_{12}$-$C_{14}$) sulfonate | 8.0 |
| Lauric isopropanolamide (foam booster and stabilizer) | 1.0 |
| Perfume | 0.7 |
| | 100.0 |

This composition provides a bath pH of about 7.0.

| EMOLLIENT BUBBLE BATH | |
| --- | --- |
| Component | Parts by Weight |
| Prilled urea | 96.2 |
| Isopropyl palmitate | 2.0 |
| Alpha olefin ($C_{12}$-$C_{14}$) sulfonate | 1.0 |
| Perfume | 0.8 |
| | 100.0 |

| EMMOLLIENT BUBBLE BATH WITH DEODORANT | |
| --- | --- |
| Component | Parts by Weight |
| Prilled urea | 89.0 |
| 2,4,4'trichloro-2'-hydroxy-diphenyl ether (germicide) | 0.2 |
| Isopropyl myristate | 2.0 |
| Alpha olefin ($C_{12}$-$C_{14}$) sulfonate | 8.0 |
| Perfume | 0.8 |
| | 100.0 |

These products can have dyes added thereto to provide any color desired.

The invention is defined in the claims which follow.

We claim:

1. A bath bead composition comprising at least 50% by weight of beads of prilled urea, said beads having absorbed therein from 0.5-10% by weight of an oily emollient, and said beads being dyed with water soluble dye.

2. A bath bead composition as recited in claim 1 in which said composition provides an approximately neutral pH in water.

3. A bath bead composition as recited in claim 1 in which said prilled urea constitutes at least 85% of the composition.

4. A bath bead composition comprising at least 50% by weight of beads of prilled urea, said beads having absorbed therein from 0.5-10% by weight of an oily emollient, said composition including from 0.1-3% by weight of germicide.

5. A bath bead composition comprising at least 50% by weight of beads of prilled urea, said beads having absorbed therein from 0.5-10% by weight of an oily emollient, and from 2-15% by weight of a foaming anionic surfactant being present in said composition.

6. A bath bead composition as recited in claim 5 in which said prilled urea constitutes at least 80% of the composition.

7. A bath bead composition as recited in claim 5 in which said foaming surfactant is a solid sulfate or sulfonate surfactant.

8. A bath bead composition as recited in claim 7 in which said surfactant is $C_{12}$-$C_{14}$ alpha olefin sulfonate.

9. A method of producing a dyed bath bead composition comprising mixing urea beads with water soluble dye in the form of a dry powder, said urea beads containing absorbed or adsorbed water to pick up said water soluble dye.

* * * * *